(12) United States Patent
Shaklai et al.

(10) Patent No.: US 7,323,295 B2
(45) Date of Patent: Jan. 29, 2008

(54) METHOD FOR EXTENDED STORAGE OF VIABLE AND PATHOGEN-SAFE BLOOD AND BLOOD COMPONENTS USING CARBON MONOXIDE

(75) Inventors: Nurith Shaklai, Tel Aviv (IL); Matityahu Shaklai, Tel Aviv (IL)

(73) Assignee: Safetin Ltd., Tel Aviv (IL)

( * ) Notice: Subject to any disclaimer, the term of this patent is extended or adjusted under 35 U.S.C. 154(b) by 375 days.

(21) Appl. No.: 10/716,625

(22) Filed: Nov. 20, 2003

(65) Prior Publication Data
US 2004/0109903 A1    Jun. 10, 2004

Related U.S. Application Data

(63) Continuation-in-part of application No. PCT/IL03/00375, filed on May 8, 2003.

(51) Int. Cl.
*A01N 1/02* (2006.01)
(52) U.S. Cl. .......................................................... 435/2
(58) Field of Classification Search ..................... None
See application file for complete search history.

(56) References Cited

U.S. PATENT DOCUMENTS 5,476,764 A * 12/1995 Bitensky ........................ 435/2

OTHER PUBLICATIONS

Amersi et al., "Ex Vivo Exposure to Carbon Monoxide Prevents Hepatic Ischemia/Reperfusion Injury Through p38 MAP Kinase Pathway", Hepatology 35 (4) : 815-823 (2002).*
Brune et al., "Inhibition of Platelet Aggregation by Carbon Monoxide is Mediated by Activation of Guanylate Cyclase", Molecular Pharmacology 32 : 497-504 (1987).*

\* cited by examiner

*Primary Examiner*—Sandra E. Saucier
(74) *Attorney, Agent, or Firm*—Mark M Friedman

(57) ABSTRACT

A method for inhibiting bacterial growth in whole blood and/or blood components, which may therefore also be used to extend the storage time for the whole blood and/or blood components, through treatment with carbon monoxide. This method is preferably used for the preservation of platelets, which are both particularly vulnerable to bacterial and other microbial infection, and which are also particularly suitable for use with the method of the present invention. Carbon monoxide may be present in an amount of from about 40% to about 100%. Platelets may be stored in a solution buffered by any suitable buffer, such as sodium bicarbonate. Platelet viability may be determined by measuring the ability to aggregate, for example in response to an agonist such as collagen.

18 Claims, 11 Drawing Sheets

Collagen-induced aggregation of preserved platelets

Air (day 1)

Air (day 12)

MAP (day 12)

METHOD FOR EXTENDED STORAGE OF VIABLE AND PATHOGEN-SAFE BLOOD AND BLOOD COMPONENTS USING CARBON MONOXIDE

This application is a CIP application, claiming priority from PCT Application No. PCT/IL03/00375, filed May 08, 2003, which claims priority from Israel Patent Application No. 149611, filed May 13, 2002, all of which are hereby incorporated by reference as if fully set forth herein.

FIELD OF INVENTION

The present invention is of a method for the extended storage and preservation of blood and blood components, by treating the blood and/or blood components with CO (carbon monoxide).

BACKGROUND OF THE INVENTION

Blood transfusion is a central therapeutic aid in modern medicine. It is a primary treatment in the field of emergency medicine. For this reason, since the beginning of the twentieth century, blood has been collected and stored in blood banks. Initially collected and stored as whole blood, blood which is obtained from donors is now separated into defined fractions before storage and eventual use to treat patients. These blood components are stored in closed plastic bags at temperatures ranging from −80÷C to +24÷C, depending upon the fraction. Table 1 below gives the current storage conditions of blood fractions.

TABLE 1

Storage conditions of blood components

| Component | Duration | Temperature, ° C. |
| --- | --- | --- |
| Whole blood | 24 hours | 20-24 |
| Red cells | 42 days | 4 |
| Platelets | 3-5 days | 20-24 |
| Stem cells | 10 years | −180 |
| Plasma | Several years | −20 |

Although human blood is distributed internationally, maintaining an adequate supply depends upon a number of factors, including the availability of donors, the provision of suitable collection and storage facilities, and the limited shelf-life of this biological material. Therefore, the medical community is interested in developing new procedures for extending the shelf-life of these blood components.

Theoretically, the shelf-life of preserved blood components depends upon two major factors: the time period during which the function of the blood components can be maintained in storage, and the reduction of pathogen contamination. The extended maintenance of the function of these components in storage has been achieved by adding such materials as phosphates and/or compounds to arrest undesirable biological activity such as coagulation, changing the pH balance of the storage medium, and maintaining the proper temperature for the particular component (as described with regard to Table 1 above). For certain types of blood components, reduced temperature levels are suitable for storage and also help to reduce the rate of the growth of contaminating microorganisms. However, for other components, such as platelets, reduced temperature levels may induce a loss of biological function and therefore cannot be used to reduce pathogen contamination.

Contamination of blood by pathogens has long been recognized as a significant complication of blood transfusion. Even if healthy donors are selected, and the resultant donated blood is screened for the presence of various types of pathogens, including viruses such as hepatitis and HIV, blood components which are stored for an extended period of time are vulnerable to pathogen contamination.

In order to help reduce such contamination, blood is collected from donors under aseptic conditions. Sterile closed systems are used for the collection and processing of blood components, further reducing pathogen contamination. However, the presence of bacteria in blood components is still currently the most common microbiological cause of transfusion-associated morbidity and mortality. Transfusion-associated contamination which is caused by the inadvertent intravenous infusion of pathogen contaminated platelets appears to be much more common than complications caused by contamination of red blood cells or plasma. This may be due to the fact that significant morbidity and mortality occurs when the contaminated blood product contains a sufficiently large number of bacteria ($\geq 10^6$), thereby resulting in a relatively high level of bacterial endotoxins. Since platelets cannot be stored at temperatures lower than 20° C. without risking the loss of biological function, the risk of contamination is proportionally much larger with platelets than with red blood cells. Indeed the rate of reported complications from infected platelets is greater than that of red blood cells by a 2:1 ratio.

Platelets are enucleated cells derived from bone marrow megakaryocytes. They play an important role in homeostasis, blood clotting and thrombosis. The life span for platelets in the blood circulation of the body is estimated to be about ten to twelve days. However, after five to six days of ex-vivo storage, platelets age, as evidenced by morphological signs of apoptosis such as a change in shape from discoid to spherical, and the presence of membrane blebbing. Another measurable parameter for platelet viability is the pH of the surrounding buffer; when it falls below pH 6.0, viability is lost. Another measurement of platelet viability is the leakage of enzymes. In particular, leakage of LDH (lactic dehydrogenase) is used as a parameter for loss of platelet viability.

Various studies have confirmed that pathogen contamination of platelets causes the highest level of mortality of all the different blood components and products. For allogeneic transfusions, the mortality rate for apheresis platelet transfusion was seven times higher than the risk of an adverse event following platelet concentrate transfusion, and more than three times higher than the risk following red blood cell transfusion. The risk increases to twelve times higher after platelet pool transfusion (from multiple donors) and 5.5 times higher after apheresis platelet concentrate infusion (all statistics from Perez et al., "Determinants of transfusion associated bacterial contamination; Results of the French BACTHEM Case Control Study"; *Transfusion*, 2001, vol 41, pp. 477-482; see also K. Sazama, "Bacteria in Blood for Transfusion: A Review", *Arch Pathol Lab Med*, vol 118, 1994, pp. 350-365). These studies of the risk of platelet contamination has led to the shortening of their shelf life from 7 to 5 days by the FDA in 1986. However, this short time window effectively reduces available supplies of platelets.

The medical community is therefore currently considering two options: providing blood banks with more rapid bacterial screening methods; and developing methods for the control of growth of bacteria and/or other pathogens. The former approach has a number of drawbacks, including lower sensitivity of the more rapid bacterial detection methods and increased expense. The latter approach has been explored, generally involving the destruction of the ability to replicate genetic material, as this approach is believed to be safe for the enucleated blood cells like red cells and platelets. For example, cross-linking chemicals, with and without the requirement for photoactivation, have been considered. Examples of such chemicals include psoralens 8-MOP, AMT and most recently, S-59 "inactine". These chemicals are considered to be hazardous to the human body and thus must be removed post-treatment, before the platelets can be given to a patient. Current removal methods include filtration or washing protocols in order to remove agents which are not bound in some manner to the surface of cells or proteins.

Since the removal process is time consuming and may also damage the blood cells, other less hazardous, agents have been considered. One example of such an agent is riboflavin, which upon photoactivation forms lumichrome. However, this agent has been shown to have variable effectiveness for bacterial inactivation and may even decrease platelet survival rates in autologous transfusions performed in primates, which has negative implications for its utility in promoting increased platelet storage times ("Connect with Safer Blood Products: Abstracts on Pathogen Eradication Technology", Gambro BCT Inc., USA, 2001).

None of the above preservation methods has been approved yet. Each method has a number of disadvantages, including the fact that they are often suitable only for one blood component, and that the removal methods employed may damage the blood components. Also, the preservation method itself may damage the blood components. Therefore, there is currently no suitable method for preservation of whole blood and/or blood components, which does not involve the introduction of potentially hazardous chemicals into the human body, and which does not damage the whole blood and/or blood components themselves.

Carbon monoxide (CO) is a natural product of hemoproteins degradation in the human body and chemically inert. It is known as a highly toxic gas due to its ability to replace, with high affinity, the sites for oxygen in hemoglobin. However, a growing body of scientific evidence has indicated in the last decade that the same molecule serves also basic physiological roles like transmission in the neurological system. Thus its location and quantity appears to determine whether carbon monoxide is helpful or harmful to the body.

SUMMARY OF THE INVENTION

The background art does not teach or suggest a method for preservation of platelets and other blood components which is readily reversible and which does not cause permanent damage or alteration to any part of the platelets. The background art also does not teach or suggest such a method in which a relatively non-toxic agent is used for treatment of the blood components and/or whole blood.

The present invention overcomes these deficiencies of the background art by providing a method for treatment of platelets, and optionally other blood components and/or whole blood, which is relatively non-toxic and which is also reversible. The method of the present invention involves treatment of the blood component and/or whole blood with carbon monoxide, which in the small amounts left after exposure to air is sufficiently non-toxic to be tolerated by the body (safety threshold or TLV for carbon monoxide for the human body is the inhalation of 8 hours per day of air containing 20 ppm of the gas, which is the equivalent of inhalation of air containing $10^4$ ppm/minute). Carbon monoxide is more toxic when inhaled than when present in other organs of the body. The method of the present invention enables relatively small amounts of carbon monoxide to be introduced to the human body, and optionally and more preferably includes a process for reducing the amount of carbon monoxide, or even eliminating carbon monoxide, before the treated whole blood and/or blood component is introduced to the body of the subject.

The present invention also provides a method for inhibiting bacterial growth in whole blood and/or blood components, which may therefore also be used to extend the storage time for the whole blood and/or blood components, through treatment with carbon monoxide. As described in greater detail below, this method is preferably used for the preservation of platelets, which are both particularly vulnerable to bacterial and other microbial infection, and which are also particularly suitable for use with the method of the present invention.

According to a preferred embodiment of the present invention, whole donated blood is first separated into various components, after which more preferably only the platelet fraction is treated with carbon monoxide. Alternatively, whole donated blood is treated with carbon monoxide, after which more preferably the platelet fraction is treated again with carbon monoxide. Alternatively or additionally, for either embodiment, the plasma fraction may also optionally be treated with carbon monoxide. Whole blood which has been treated with carbon monoxide may also optionally be used for transfusion to the body of the subject.

The method of treatment according to the present invention more preferably includes removing air from the container which holds the platelet fraction, and then introducing a modified atmosphere containing carbon monoxide as the major component. Optionally and preferably, up to about 10% of the modified atmosphere is oxygen. Preferably up to about 90% of the atmosphere comprises carbon monoxide, more preferably up to about 99% and most preferably about 100% of the atmosphere comprises carbon monoxide. Optionally the amount of carbon monoxide is at least about 40%. The container then is more preferably stored at the appropriate temperature for the particular blood component fraction, which as previously described may preferably be the platelet fraction, but alternatively is optionally the whole blood itself. Examples of preferred such temperatures include but are not limited to, room temperature for whole blood cells and platelets (20-24° C.); refrigeration temperatures for packed red blood cells (4° C.); −20° C. for plasma; and −180° C. for bone marrow (stem cells). Preferably, treated whole blood is stored at a suitable temperature for the present invention, such as room temperature for example.

The present invention has a number of advantages, including but not limited to, inhibition of the growth of pathogens, such as parasites, mold and bacteria; and extension of the shelf life of each fraction and also of whole blood.

CO was shown to play a role also in platelet activation as it can inhibit aggregation of platelets via binding to Guanylate Cyclase (Brune Band Ullrich, V.; Molec *Pharm*, vol 32, pp 497-504, 1987). Therefore another possible advantage of the use of CO in the present invention is the possible positive contribution of CO to preservation by preventing loss of platelet viability through ex vivo aggregation.

According to another embodiment of the present invention, there is provided a method for determining viability of at least one of whole blood and a platelet-containing fraction of blood after storage, comprising: determining ability of the at least one of whole blood and the platelet-containing fraction of blood to aggregate in response to an agonist such as collagen, wherein aggregation is a measure of viability. Preferably, at least one of whole blood and the platelet-containing fraction of blood are treated with carbon monoxide to form a treated blood product before storage. More preferably, before determining ability of the at least one of whole blood and the platelet-containing fraction of blood to aggregate in response to an agonist such as collagen, the method comprises: promoting exchange of carbon monoxide in the treated blood product with oxygen.

Although reference is made to treatment of blood components, this is for the purposes of explanation only and is not meant to be limiting in any way, as the present invention is also suitable for the treatment of whole blood.

Hereinafter, the term "blood product" refers to at least one of whole blood and a blood component, such as platelets for example.

BRIEF DESCRIPTION OF THE DRAWINGS

The foregoing and other objects, aspects and advantages will be better understood from the following detailed description of a preferred embodiment of the invention with reference to the drawings, wherein:

FIG. 2; *Bacilus Cereus;*

FIG. 3; *E. Coli;*

FIG. 4; *Pseudomonas Aeraginosa:*

FIG. 5; *Bulkholderia Cepasea;*

FIG. 6; *Staphilococcus Aereus;*

DESCRIPTION OF PREFERRED EMBODIMENTS

Figure 1:
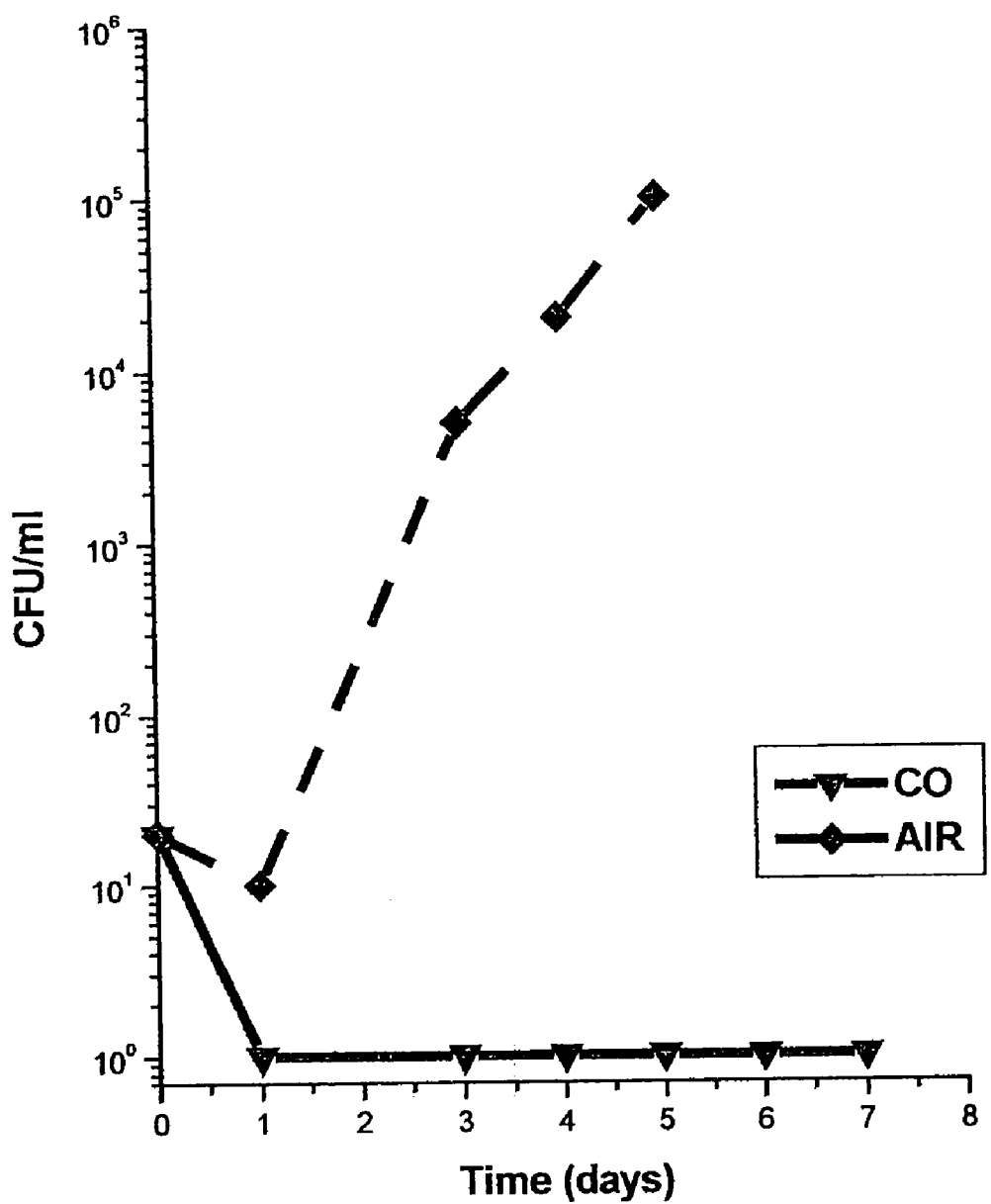
FIG. 1 shows the growth of inoculated Yersinia Enterocolitica in whole blood kept under carbon monoxide atmosphere (CO) or regular air (AIR)

The present invention is of a method for treatment of platelets, and optionally other blood components, which is relatively non-toxic and which is also reversible. The method of the present invention involves treatment with carbon monoxide, which in small amounts is sufficiently non-toxic to be tolerated by the body, as previously described.

The present invention also provides a method for inhibiting bacterial growth in blood components, which may therefore also be used to extend the storage time for these blood components, through treatment with carbon monoxide. As described in greater detail below, this method is preferably used for the preservation of platelets, which are both particularly vulnerable to bacterial and other microbial infection, and which are also particularly suitable for use with the method of the present invention.

According to a preferred embodiment of the present invention, whole donated blood is first separated into various components, after which more preferably only the platelet fraction is treated with carbon monoxide.

According to another preferred embodiment of the present invention, the whole donated blood is first treated with carbon monoxide, after which the blood components are optionally separated. Alternatively, the whole treated blood may be used for administration to a subject after removal of carbon monoxide. The blood components may optionally be treated with carbon monoxide again before storage.

Regardless of the method of treatment with carbon monoxide, optionally and more preferably, the treated whole blood and/or blood components may be exposed to light such as 400 nm and above, most preferably in the presence of oxygen. Such illumination promotes the exchange of carbon monoxide with oxygen (see for example Brune Band Ullrich, V.; *Molec Pharm*, vol 32, pp 497-504, 1987).

The method of treatment according to the present invention more preferably includes removing air from the container which holds the platelet fraction, and then introducing a modified atmosphere containing carbon monoxide as the major component (component in the majority), such that more preferably below about 1% oxygen is present in the modified atmosphere. Preferably, up to about 100% of the atmosphere comprises carbon monoxide, more preferably up to about 99% and most preferably up to about 90% of the atmosphere comprises carbon monoxide. Optionally the amount of carbon monoxide is at least about 40%. The container then is more preferably stored at the appropriate temperature for the particular blood component fraction, which as previously described may preferably be the platelet fraction, but alternatively is optionally the whole blood itself. Examples of such temperatures include but are not limited to, room temperature for whole blood cells and platelets (20-24° C.); refrigeration temperatures for packed red blood cells (4° C.); −20° C. for plasma; and −180° C. for bone marrow (stem cells).

For treatment of a subject with the treated blood, optionally gas exchange of oxygen for carbon monoxide is promoted before administration to the subject, for example by opening the bag or other container holding the blood or blood component and allowing such a gas exchange with the surrounding air. Alternatively, the container could optionally remain sealed, while an atmosphere containing oxygen but no carbon monoxide is introduced.

Another optional but preferred method involves the illumination of the blood and/or blood component, more preferably with light having a wavelength of 400 nm and above in the presence of an atmosphere containing pure oxygen or a high concentration thereof, or air. More preferably, such treatment is performed with agitation of the blood and/or blood component, most preferably for about 20 minutes in the presence of oxygen or about 35 minutes in the presence of air. Any red blood cells required for transfusion particularly preferably undergo such treatment before administration to the subject, as otherwise their oxygen-carrying capacity may be reduced.

Materials and Methods

A. Preparation of Treated Blood Components

Freshly drawn whole blood was obtained from a human donor under sterile conditions, and stored in gas impermeable bags having a volume of at least 1.5 times that of the blood volume. The gas environment (or atmosphere) in the bag was then replaced by an atmosphere containing sterile CO by applying a low level vacuum with a water pump of 20 mm Hg. CO was immediately flushed through a 0.25 micron sterile filter. The bag was sealed and agitated for 15 minutes to allow equilibration. This procedure was repeated three times thereby exchanging the atmosphere in the bag and blood with CO. Saturation with carbon monoxide can be identified in hemoglobin in samples of the treated blood according to typical changes of the light absorption spectrum of the hemoglobin in the visible region by a shift from 577 nm (typical of oxy-hemoglobin) to 569 nm (typical of carbomonoxy-hemoglobin).

The treated blood was kept at room temperature on a shaker until tested (as described in greater detail below) or alternatively until fractionation of the treated blood into blood components (red blood cells, plasma, platelets) using regular blood bank procedures. For further preservation, fractions were separately treated.

B. Preparation of Platelets as PRP or PC for Preservation

PC fractions were identically prepared from CO pretreated or untreated blood by consecutive centrifugation in a sterile environment using blood bank conditions. Bicarbonate (4% of PC volume) is than added from a stock solution of 750 mM while agitation to yield a final bicarbonate concentration of 30 mM. Next, the PC is treated with CO in a similar manner to whole blood. Alternatively, rather than applying a vacuum, the containers were flushed for 10 min. with sterile CO while agitating the containers, which were then sealed. The containers were allowed to stay at room temperature of 20-24° C. PRP platelets were treated similarly.

Control blood samples were packed under air in the same containers without any additional treatment allowing air transfer. In some experiments control of inert gas like nitrogen were used to exchange the air in the same manner as CO.

C. Bacterial Growth

The method of the present invention was shown to be useful for inhibition of bacterial growth, by inoculating the platelet-containing fractions with various strains of gram negative and gram positive bacterial pathogens. The types of bacteria and the amount inoculated are described in greater detail below with regard to the drawings.

Whole blood or its factions were inoculated with pathogenic bacteria. Growth of the bacteria at room temperature was followed under different atmospheres (gas environments). The blood fractions were platelets in plasma (PRP); concentrated platelets (PC) as currently stored in blood banks after removal of about three quarters of the plasma and the cell-free blood plasma.

FIG. 1 shows growth in whole blood of a pathogen, *Yersinia*, which requires iron for growth and thus grows rapidly in hemoglobin containing media. *Yersenia Enterocolitica* strain was received from ATCC and grown in a specific rich medium. About 20 bacteria per ml were inoculated in fresh blood samples which were stored at room temperature. The blood was stored under CO atmosphere and as controls, samples of the same blood were stored under air. In FIG. 1, a representative example is shown. Growth was fast under air but was completely inhibited when the same blood was kept under nitrogen. To free the packed blood of CO, the sealed packages were opened to air for a few minutes. To further release heme-bound CO, photolysis was used by irradiation of light at 400 nm and above.

For FIGS. 2-6, platelets were stored as PRP with agitation at room temperature (20-24° C.) in a blood bank rocking plane as for regular blood bank under air with gas exchange option (AIR); or sealed under nitrogen atmosphere ($N_2$) or carbon monoxide atmosphere (CO). All gases were filtered through a sterile 0.25 microns filter. All bacteria were identified ATCC strains. The amount of inoculated bacteria was adjusted to a range of 10-100 CFU/ml before inoculation, in which the exact final number of bacteria was been measured by plating the stock on suitable agar plates allowing growth and counting (the final initial counts are given in each case).

Figure 2:
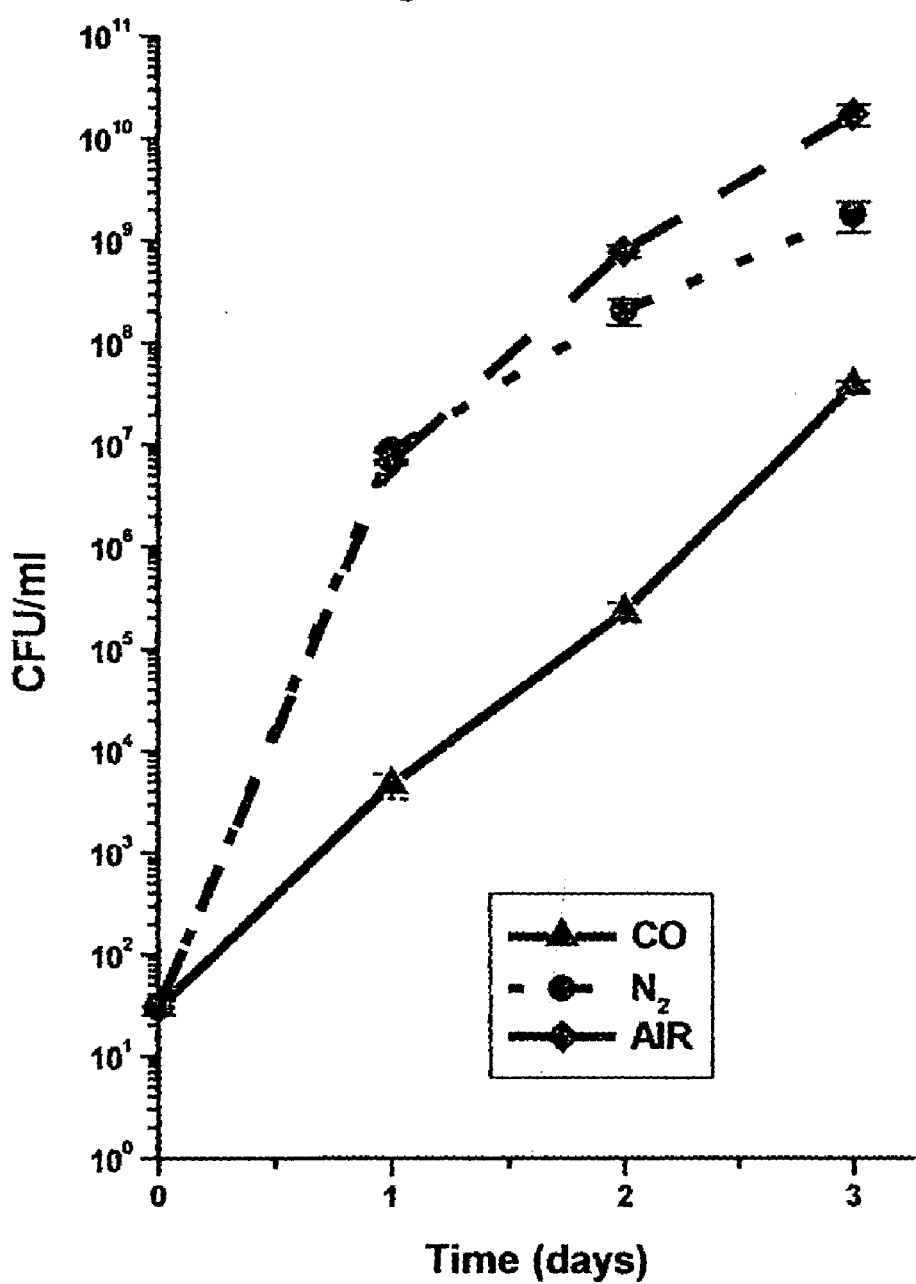
FIGS. 2-6; show the growth of inoculated identified bacteria in platelets suspended in plasma as PRP under regular air (AIR), nitrogen atmosphere ($N_2$) or (CO); Growth of the following bacteria is shown in each figure.
Figure 3:
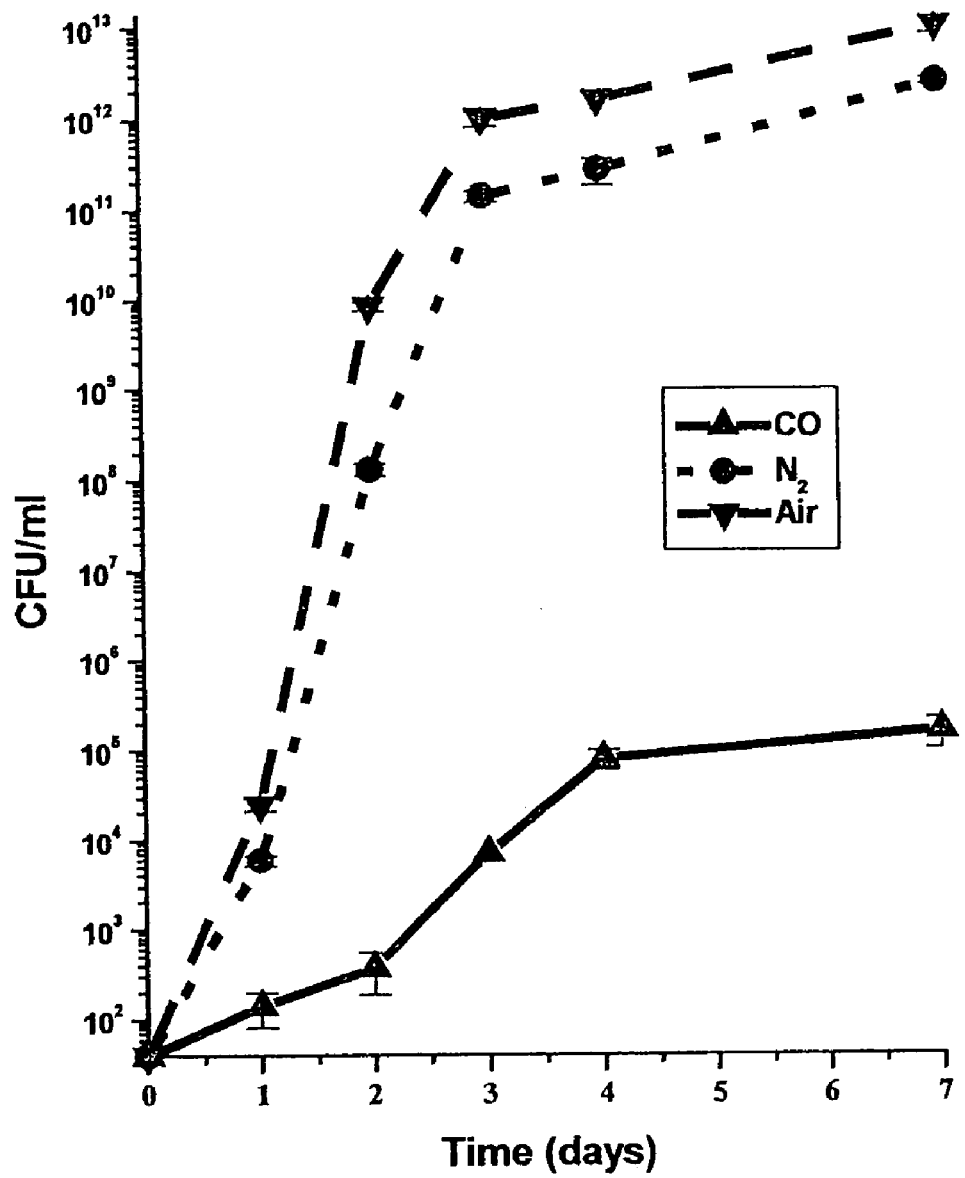
Figure 4:
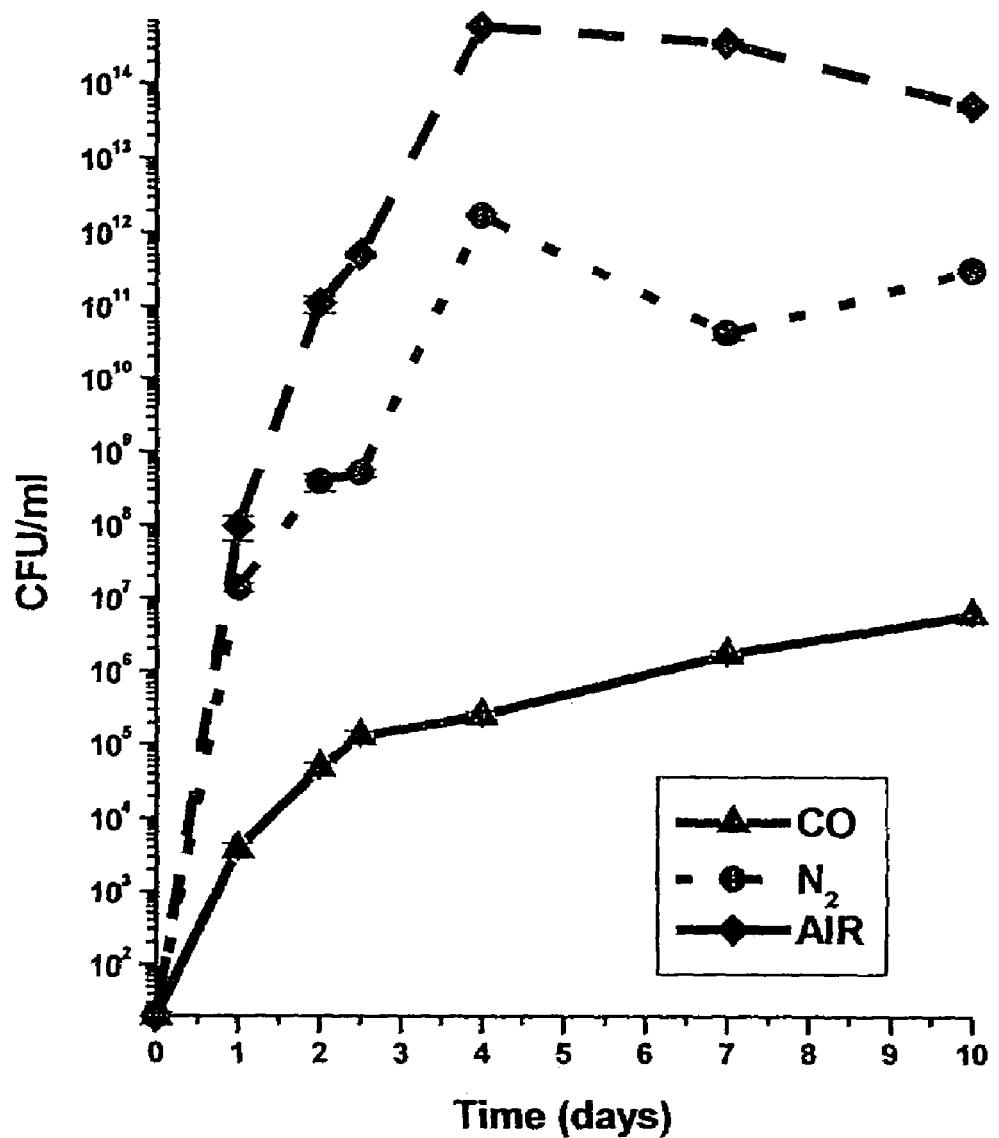
Figure 5:
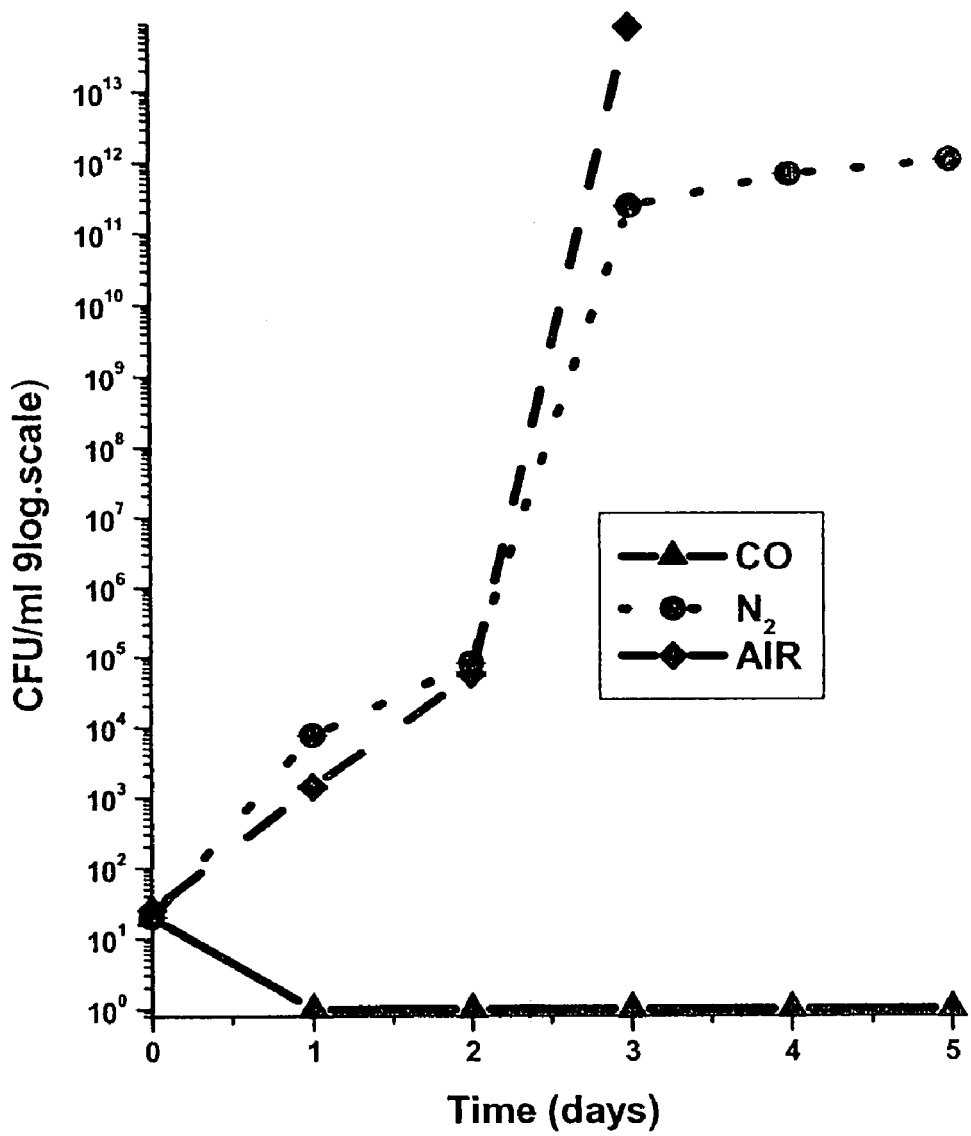
Figure 6:
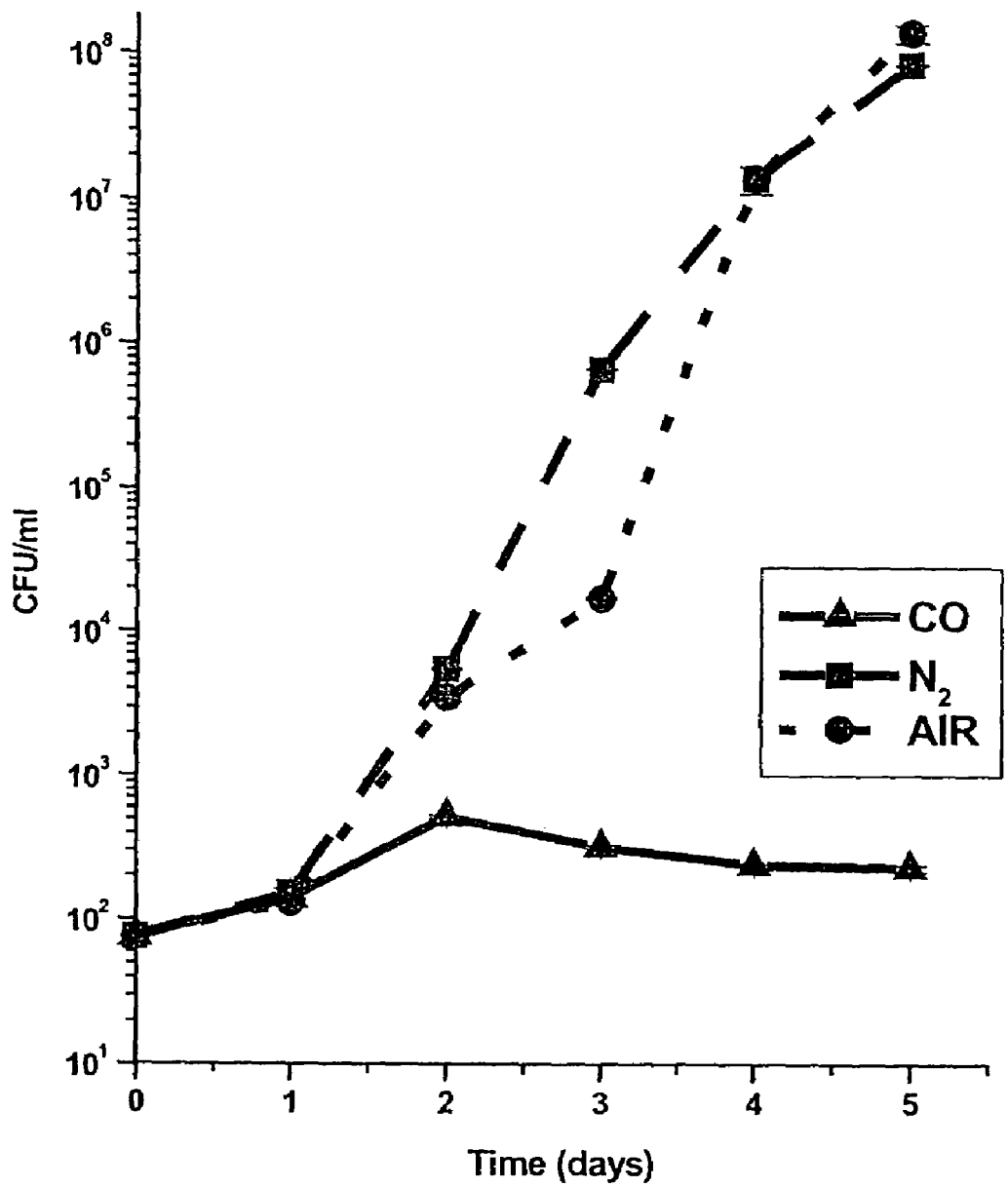

FIG. 2 shows the growth of *Bacilus cereus* in PRP, inoculated at 18 CFU/ml. FIG. 3 shows the growth of *E. coli* (strain O157) in PRP, inoculated at 25 CFU/ml. FIG. 4 shows the growth of *Pseudomonas aeraginosa* in PRP, inoculated at 16 CFU/ml. FIG. 5 shows the growth of *Bulkholderia cepasea* in PRP, inoculated at 12 CFU/ml. FIG. 6 shows the growth of *Staphilococcus aereus* in PRP, inoculated at 18 CFU/ml.

Figure 7:
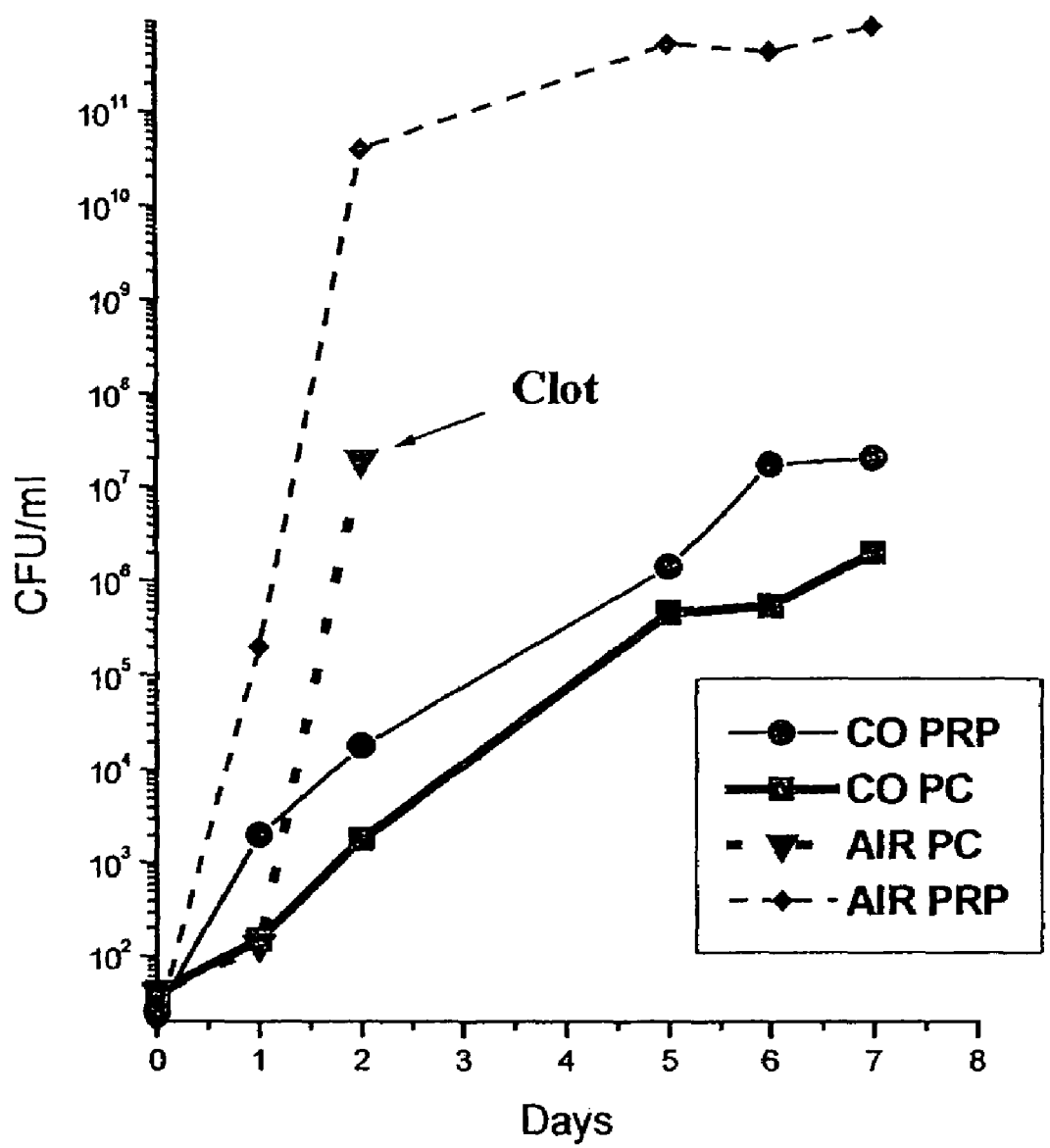
FIG. 7 compares the growth of *Salmonella Thyphimurium* in platelets suspended in plasma as PRP and PC after treatment with AIR or CO.

FIG. 7 compares the growth of *Salmonella thyphimurium* in PRP or PC fractions, with an initial inoculation ~20 CFU/ml (actual count at time zero was 16 CFU/ml or 32 CFU/ml, respectively). The growth in the two different preparations of platelets is similar. However, it should be noted that under conditions which promote the rapid growth of bacteria (AIR), a clot of platelets is formed, which does not enable a homogenous sample to be taken for counting the level of bacteria.

Figure 8:
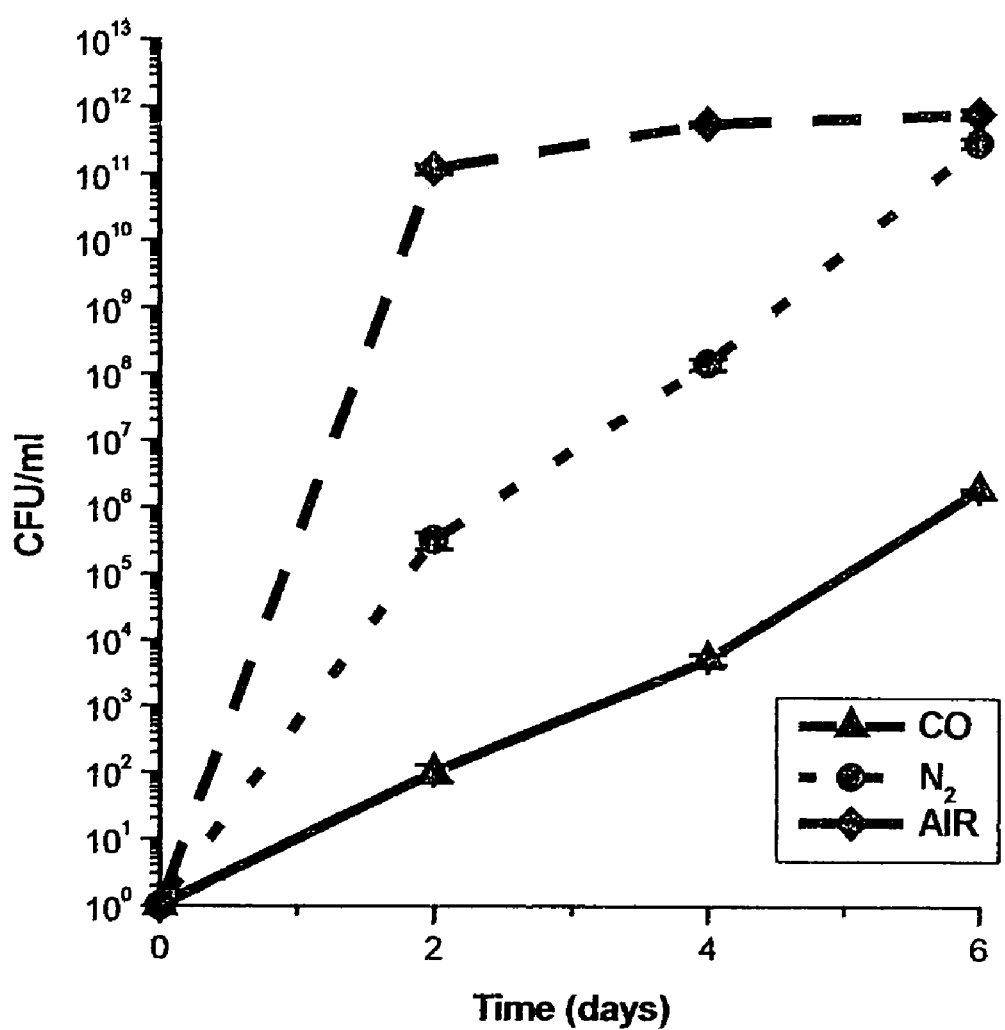
FIG. 8 shows the growth of *Salmonella thyphimurium* in cell-free plasma under similar conditions.

FIG. 8 compares the growth of *Salmonella thyphimurium* in cells-free plasma under AIR, N2 and CO.

D. Platelet Viability Testing

The viability of the platelets under storage was tested in the form of PC because platelets are currently stored in this form, in order to be able to store and use the extra plasma in PRP separately. However, the PC environment lacks both red cells and plasma, such that platelets in this environment are more sensitive than in the PRP form to loss of viability. Without wishing to be limited to a single hypothesis, platelets in the form of PC may experience changes in pH, and therefore may lose the necessary pH neutrality of the environment. The viability of platelets stored as PC was investigated according to two parameters: drop of pH of the environment, and loss of membrane integrity of the cells themselves, leading to leakage of cellular proteins.

With regard to pH value, platelets have been shown to deteriorate under pH conditions which deviate from neutrality, particularly low pH values (values less than about 6.0). Anaerobic metabolism of the in the platelets tends to result in high levels of lactic acid, and may therefore affect platelet viability. Storage of platelets under low or no oxygen conditions may be expected to reduce platelet viability for this reason. Thus, the pH value of the PC and PRC fractions during preservation with regular methods (allowing free exchange of gases) was compared to the pH value obtained after treatment with carbon monoxide according to the present invention.

Figure 9:
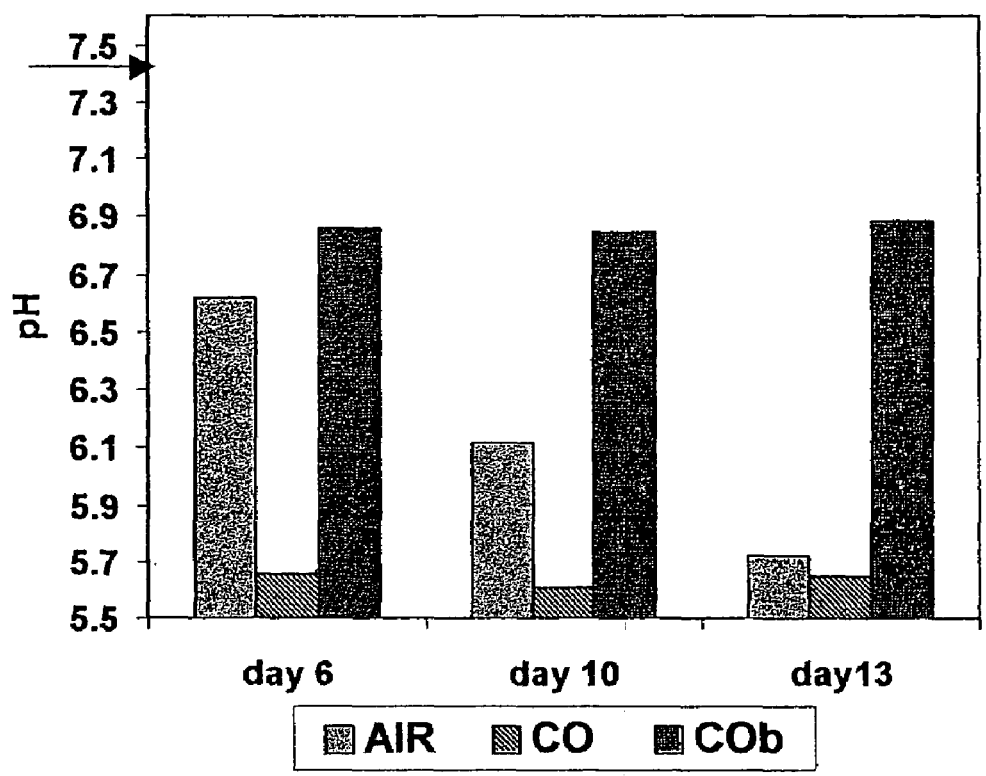
FIG. 9 compares the changes in pH during storage of platelets as PC under air and carbon monoxide atmospheres in the absence or presence of additional bicarbonate buffer.

FIG. 9 compares the changes in pH during storage of platelets concentrate (PC) under AIR and CO in which to part of the packages stored under CO aliquots of sterile bicarbonate solution to yield final concentration of 30 mM was added (COb).

With regard to leakage of LDH, cell viability can also be evaluated according to membrane integrity. LDH (lactic dehydrogenase) is a stable enzyme which is normally active inside cells; when these cells have loss of membrane integrity, LDH is leaked outside the cells, such that higher levels of LDH activity are correlated with reduced platelet viability. The presence of LDH activity in platelet-free solution samples was measured in order to assess the viability of the platelet-containing fractions from which the samples were taken.

The viability of the platelets was then tested according to pH value of the solution in which they were contained, and also according to LDH activity, since as previously noted, leakage of LDH is an indicator for the lack of platelet viability.

Figure 10:
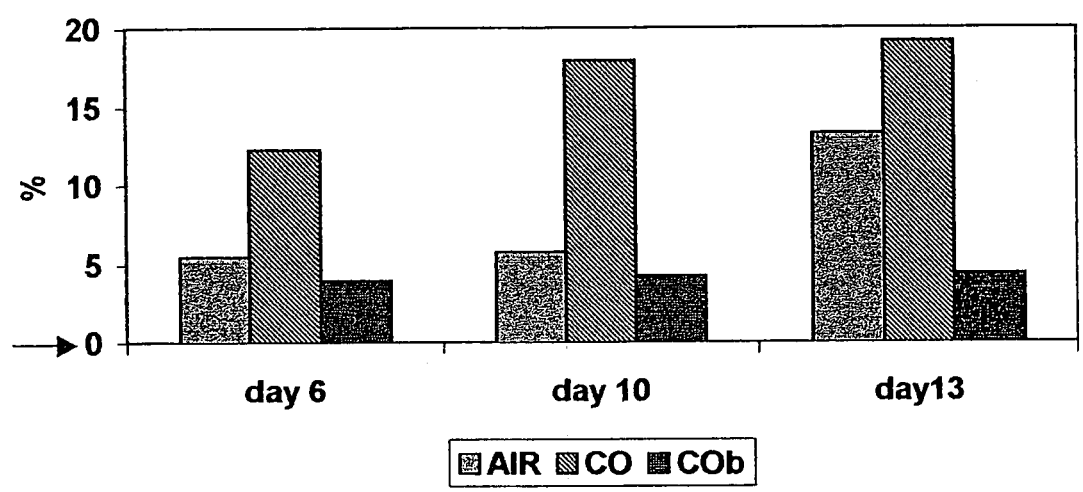
FIG. 10 compares the leakage of LDH from platelets stored as PC under air and carbon monoxide atmospheres in the absence or presence or additional bicarbonate buffer.

FIG. 10 shows leakage of the enzyme LDH from sterile platelets stored as PC under AIR (exchangeable with room gases) and CO. Part of the packages stored under CO aliquots of sterile bicarbonate solution to yield final concentration of 30 mM was added (COb) (abbreviations as for FIG. 9).

FIG. 11 shows the ability of platelets to aggregate. An assessment of the potential of platelets to form aggregates upon activation by an agonist, preferably collagen, a typical physiological agonist, was performed, to determine the potential effect of carbon monoxide on this physiological function of platelets. The assay was performed as follows.

Fresh blood bank platelets, prepared as platelet concentrates (PC), were used. Each PC unit was divided. One part was stored without carbon monoxide treatment, which is the current method of preserving PC in blood banks. The other portion was sealed under carbon monoxide as previously described. Samples were preserved under sterile conditions at 20-23° C., while shaking gently. The ability of platelets to aggregate upon activation by collagen as an agonist was tested daily using a kit by Helena Laboratories (USA), called the Plateletworks kit. To allow platelet count and reduce anticoagulant activity, the PC was diluted 1:10 with the physiological buffer PBS pH 7.3. The whole individual platelets present were counted prior and after addition of the agonist, for this example collagen.

Platelets stored under carbon monoxide did not form aggregates upon exposure to collagen when tested immediately after being exposed to air, but regained their ability to aggregate in response to collagen when carbon monoxide was replaced by air. Therefore, the stored PC samples (control and stored under carbon monoxide) were tested for their ability to aggregate following two hours shaking under air after being removed from storage.

Results and Discussion

As shown in FIG. 1, carbon-monoxide completely inhibited pathogen growth in whole blood. In platelet rich plasma, carbon monoxide significantly inhibited (FIGS. 2-4, 6,7) or even eliminated (FIGS. 1 and 5) bacterial growth. By contrast, nitrogen had little or no effect on bacterial growth, in comparison to regular air conditions (freely exchangeable gases).

FIG. 7 shows that bacterial growth was inhibited in platelets stored as PRP or PC in comparison to regular air conditions (AIR). Growth of facultative bacteria kept under CO atmosphere was inhibited not only comparison to air but also when compared to nitrogen (FIGS. 2-7). This indicated that CO inhibits growth of the bacteria specifically and not due to slower energy production rate of facultative bacteria with anaerobic metabolism.

The inhibition of pathogen growth was maintained when plasma alone was used as their source of nutrition. Therefore if preservation of plasma is performed under non-refrigerated conditions, sterility may also optionally be maintained through treatment.

To examine the viability of the stored platelets, the pH of the preserved cells as well as leakage of LDH (lactic dehydrogenase) was followed, because leakage of LDH from platelets is an established parameter for loss of viability. pH was maintained well in platelets stored as PRP but dropped beyond neutral in platelets stored under either nitrogen (not shown) or CO (FIG. 9). Reduction of pH is expected to result under anaerobic metabolism. To assist the ability of platelets to maintain their pH, 30 mM of the natural buffer in the blood, treatment with a basic buffering substance such as bicarbonate is sufficient (FIG. 9).

Regarding LDH activity in supernatant, again when platelets were stored as PRP, leakage of LDH was equal or even somewhat lower than under air (data not shown). The viability of platelets in PC, stored under CO, was lost much faster than stored in air (FIG. 10). Because a similar reduction in shelf-life occurred under nitrogen (not shown), without wishing to be limited by a single hypothesis, it is possible that the failure of PC to maintain the neutral pH was the cause. Viability of platelets as exhibited by leakage of LDH was maintained. FIG. 10 shows that LDH activity in the supernatant, a measure of leakage, was lowest, and therefore platelet viability was presumably highest, in platelets stored under carbon monoxide in a solution containing sodium bicarbonate. Platelets stored under regular air conditions and carbon monoxide alone showed similar, high levels of LDH activity, thereby indicating that such storage resulted in a loss of platelet viability.

Figure 11A:
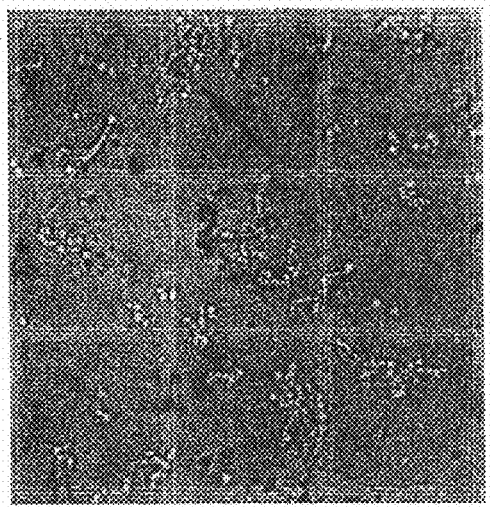
FIGS. 11A-C show the response of platelets to collagen immediately after preparation (control, FIG. 11A); after long-term storage without treatment with carbon monoxide according to the present invention (FIG. 11B); and after long-term storage and treatment with carbon monoxide according to the present invention (FIG. 11C).
Figure 11B:
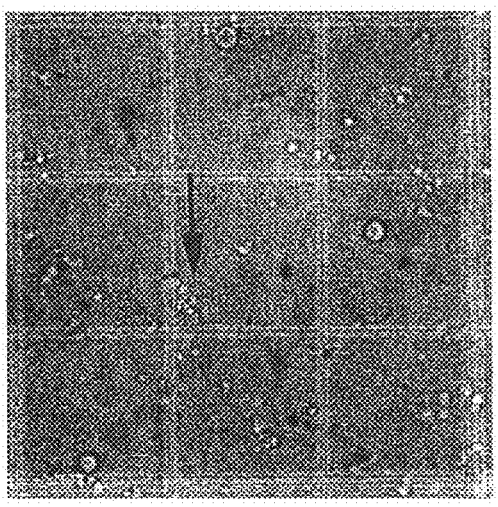
Figure 11C:
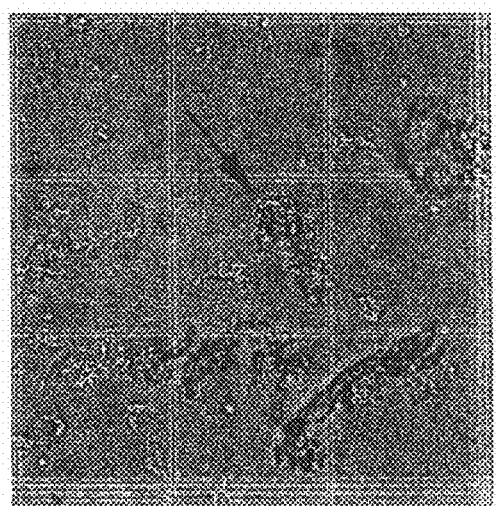

As shown with regard to FIGS. 11A-11C, a larger fraction of platelets stored under carbon monoxide was able to form aggregates as compared to platelets from the same PC unit that were stored under air.

FIG. 11A (left) shows collagen induced platelets from freshly prepared PC (day 1). FIG. 11B (middle) shows collagen induced platelets from PC stored under air at day 11. FIG. 11C (right) shows collagen induced platelets from PC stored under carbon dioxide at day 11.

Conclusions

Based upon the above results, the method of the present invention for platelet treatment with carbon monoxide is clearly able to reduce or eliminate bacterial growth in platelet-containing fractions. Similar results are seen regardless of whether the platelet fractions are PRP or PC type fractions. However, this result is not due to anaerobic conditions, as nitrogen failed to result in any significant inhibition of bacterial growth.

Platelet viability was most clearly maintained in solutions which also contained sodium bicarbonate, a basic buffering substance, in addition to treatment with carbon monoxide as long as the pH was maintained by increased buffer capacity in the form of additional sodium bicarbonate. The present invention represents the first use of carbon monoxide to retard bacterial growth in platelet-containing fractions, as well as the first demonstration that such treatment could also maintain platelet viability.

Therefore, a preferred aspect of the method of the present invention includes treatment with a basic buffering substance such as sodium bicarbonate or a similar substance, before treatment with carbon monoxide.

The method of the present invention also clearly differs from previous attempts to use carbon monoxide to extend storage time of other biological materials, in that the present invention represents the first use of carbon monoxide to retard bacterial growth in platelet-containing fractions, as well as the first time that such treatment could also maintain platelet viability.

For example, U.S. Pat. No. 6,042,859 describes a method for preserving meat with carbon monoxide, by exposing raw meat to a pure carbon monoxide atmosphere. However, this patent does not teach or suggest the use of carbon monoxide for any type of blood product treatment.

U.S. Pat. Nos. 5,476,764 and 6,270,829 describe a method for using carbon monoxide to extend the shelf-life of refrigerated red blood cells. However, these disclosures only teach the use of carbon monoxide to bind to hemoglobin, in order to prevent red blood cell aging. No teachings are provided for inhibiting bacterial growth. Furthermore, no teachings are provided for the use of carbon monoxide in any other type of blood product, which is not surprising, since only red blood cells contain hemoglobin. The disclosed method requires reversal of the treatment before the red blood cells can be introduced into a patient, which is not required as part of the method of the present invention. Also, the disclosures do not teach or suggest the use of carbon monoxide to extend the storage time of platelets by inhibiting bacterial growth, nor do they teach or suggest the addition of a pH buffering substance to further extend the viability of platelets stored under a carbon monoxide atmosphere.

According to a preferred embodiment of the present invention, there is provided a method for determining viability of at least one of whole blood and a platelet-containing fraction of blood after storage. The method preferably includes determining the ability of the at least one of whole blood and the platelet-containing fraction of blood to aggregate in response to an agonist such as collagen for example, wherein aggregation is a measure of viability.

Preferably, at least one of whole blood and the platelet-containing fraction of blood are treated with carbon monoxide to form a treated blood product before storage. Optionally any of the previously described treatment methods with any previously described concentration of carbon monoxide and/or other gases may be used for the atmosphere for the treatment. More preferably, before determining ability of the at least one of whole blood and the platelet-containing fraction of blood to aggregate in response to collagen, the method comprises: promoting exchange of carbon monoxide in the treated blood product with oxygen.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method for ex-vivo treatment of platelets, comprising treating platelets with carbon monoxide, and further comprising, after said treating step, the step of promoting atmospheric exchange of air for carbon monoxide in said treated platelets.

2. The method of claim 1, wherein said treating comprises placing the platelets in an atmosphere containing at least about 40% carbon monoxide.

3. The method of claim 2, wherein said atmosphere comprises carbon monoxide at a concentration in the range of about 40% to about 100%.

4. The method of claim 1, further comprising the step of storing said treated platelets at a suitable temperature, wherein viability of the stored, treated platelets is retained.

5. The method of claim 1, wherein said promoting step is performed by exposing said treated platelets to air for a sufficient time to allow gas exchange to occur.

6. The method of claim 1, wherein said air comprises oxygen.

7. The method of claim 1, wherein said treating step optionally further comprises adding a pH buffering substance to said platelets.

8. The method of claim 7, wherein said pH buffering substance comprises bicarbonate.

9. The method of claim 1, wherein said platelets includes at least one of PRP and PC fractions.

10. A method for inhibiting pathogen growth in a platelet-containing fraction, comprising treating the platelet-containing fraction with carbon monoxide for a sufficient amount of time to inhibit pathogen growth, further comprising, after said treating step, the step of promoting atmospheric exchange of air for carbon monoxide in said treated platelet-containing fraction.

11. The method of claim 10, wherein said platelet-containing fraction includes at least one of PRP and PC fractions.

12. The method of claim 10, wherein said treating comprises placing the platelet-containing fraction in an atmosphere containing at least about 40% carbon monoxide.

13. The method of claim 12, wherein said atmosphere comprises carbon monoxide at a concentration in the range of about 40% to about 100%.

14. The method of claim 10, further comprising the step of storing said treated platelet-containing fraction at a suitable temperature to preserve viability of the platelets.

15. The method of claim 10, wherein said promoting step is performed by exposing said treated platelet-containing fraction to air for a sufficient time to allow gas exchange to occur.

16. The method of claim 10, wherein said air comprises oxygen.

17. The method of claim 10, wherein said treating step optionally further comprises adding a pH buffering substance to said platelet-containing fraction.

18. The method of claim 17, wherein said pH buffering substance comprises bicarbonate.

* * * * *